US006644851B1

(12) United States Patent
Kumagai

(10) Patent No.: US 6,644,851 B1
(45) Date of Patent: Nov. 11, 2003

(54) ROENTGENOGRAM IMAGE CAPTURING SYSTEM

(76) Inventor: Yasuo Kumagai, 344-29, Imaichi, Imaichi-shi, Tochigi (JP)

(*) Notice: Subject to any disclaimer, the term of this patent is extended or adjusted under 35 U.S.C. 154(b) by 699 days.

(21) Appl. No.: 09/585,547

(22) Filed: Jun. 2, 2000

(30) Foreign Application Priority Data

Jun. 24, 1999 (JP) ............................................ 11-178361
Mar. 27, 2000 (JP) ....................................... 2000-085603

(51) Int. Cl.[7] ................................................ G03C 5/16
(52) U.S. Cl. ...................................... 378/167; 378/181
(58) Field of Search ................................ 378/167, 181; 382/132

(56) References Cited

U.S. PATENT DOCUMENTS 5,068,739 A * 11/1991 Filo ............................. 348/96
5,321,681 A * 6/1994 Ramsay et al. ................ 369/69

FOREIGN PATENT DOCUMENTS

| JP | 2-32808 | 3/1990 |
|---|---|---|
| JP | 4-363764 | 12/1992 |
| JP | 5-28234 | 2/1993 |
| JP | 9-34913 | 2/1997 |
| JP | 10-162125 | 6/1998 |

OTHER PUBLICATIONS

English Language Abstract of JP No. 4–363764 Dec. 16, 1992.
English Language Abstract of JP No. 2–32808 Mar. 1, 1990.
English Language Abstract of JP No. 5–28234 Feb. 5, 1993.
English Language Abstract of JP No. 9–34913 Feb. 7, 1997.
English Language Abstract of JP No. 10–162125 Jun. 19, 1998.

* cited by examiner

Primary Examiner—David V. Bruce
(74) Attorney, Agent, or Firm—Venable LLP; Andrew C. Aitken

(57) ABSTRACT

A system, apparatus, method and computer program product for capturing a roentgenogram image comprises: a typical diagnostic type of roentgenogram film projector for holding a roentgenogram film of a predetermined part of patient's body to project the roentgenogram image thereon; an image capturing unit disposed face to face with the projector for capturing the projected roentgenogram image to produce a digital image data; and a personal computer. The computer has: a console unit having a displaying unit capable of displaying the roentgenogram image on the basis of the digital image data on a predetermined roentgenogram viewer screen; an inputting unit for allowing an operator to specify the patient corresponding to the roentgenogram image displayed on the roentgenogram viewer screen; a storage device capable of storing therein a plurality of the digital image data on the roentgenogram images; and a controlling unit operable to relate the plurality of the digital image data on the roentgenogram images with the specified patient to sort the plurality of the digital image data by the patient, and store the sorted digital image data in the storage device.

16 Claims, 10 Drawing Sheets

FIG. 7
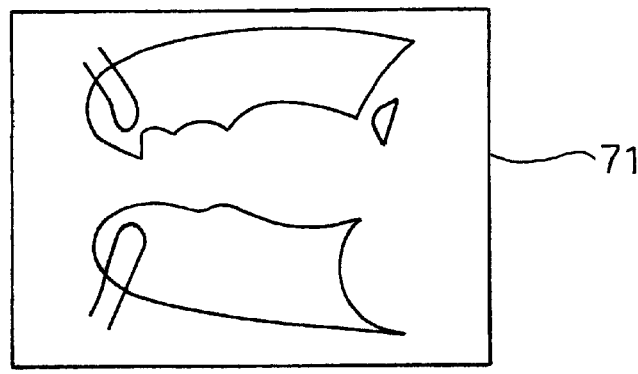
71
↓ BRIGHTNESS CONTROL
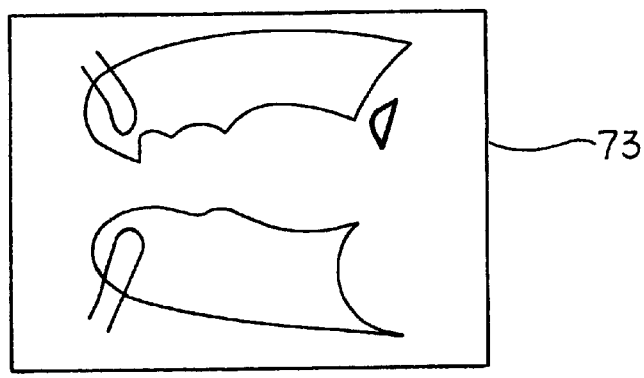
73
↓ QUARTER TURN IMAGE TO RIGHT
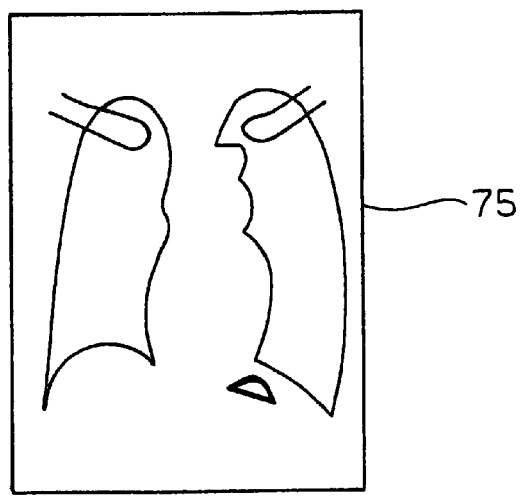
75

F I G. 8
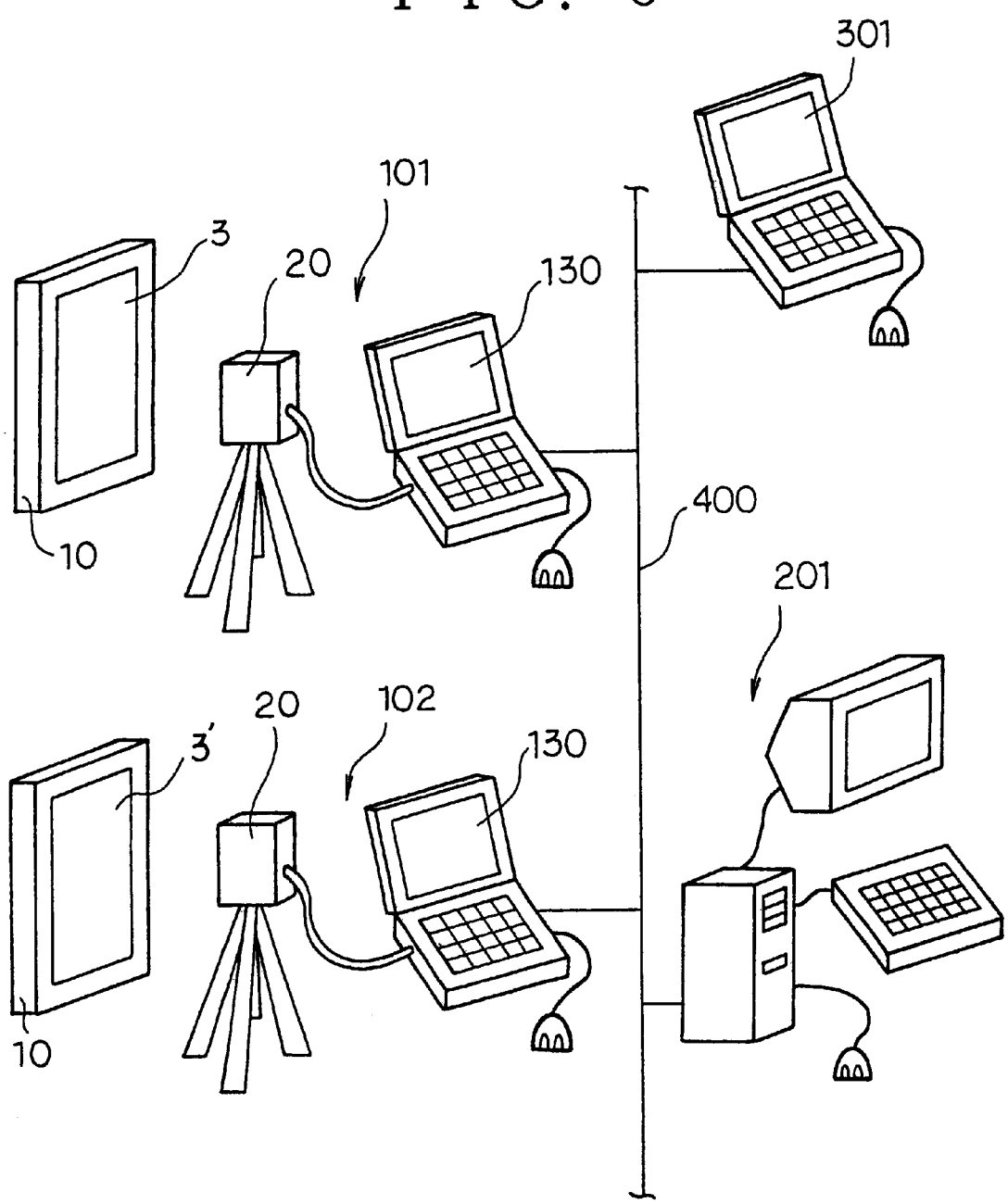

ROENTGENOGRAM IMAGE CAPTURING SYSTEM

BACKGROUND OF THE INVENTION

1. Field of the Invention

The present invention relates to a system, apparatus, method and computer program product for capturing an image of the roentgenogram film, and more particularly, to a system, apparatus, method and computer program product for capturing an image of the roentgenogram film to produce a digital image data to display the roentgenogram image on the screen.

2. Description of the Related Art

The roentgenogram film of patient's body is available for the medical examination of the patient. It is necessary for the hospital to prepare a large medical record room enough to store an enormous amount of the roentgenogram films therein. However, there is a physical limit of the capacity of this room in the hospital. For this reason, the older roentgenogram films should be discarded after a predetermined legal obligated storage duration has been elapsed.

When the doctor examines the patient, the doctor may instruct the nurse to go searching the medical record room for the roentgenogram film corresponding to the patient to retrieve the corresponding film from the enormous amount of the roentgenogram films. This is a terrible troublesome work.

In order to solve this problem, there has been proposed a microfilm system for reducing a plurality of roentgenogram films in size to record the miniature images of the roentgenogram films on a microfilm roll. Such manner of using the microfilm, however, remains also a physical limit of the capacity of the room for containing a number of microfilm rolls. Although the microfilm is suitable to record a large number of images of the roentgenogram films thereon, it is difficult to exactly relate the large number of the roentgenogram images in the microfilm with the corresponding patients.

This work spends time and effort. Moreover, it is necessary to more spend time and effort on searching the microfilm for the desired roentgenogram image. Even if the desired roentgenogram image can be found fortunately, the miniature images of the roentgenogram films on the microfilm roll should be converted into the visible form.

Recently, there has been proposed a digital X-ray image capturing system for directly capturing an X-ray image to produce a digital image data. However, it is difficult to generally spread such digital X-ray image capturing system because the digital X-ray image capturing system is incompatible with the conventional computer network system comprising a typical X-ray capturing apparatus, a roentgenogram film projector, a host computer, and a plurality of terminals linked with the host computer through a network, in the hospital. These devices of the conventional system in the whole hospital therefore should be discarded and replaced with those of the new digital X-ray image capturing system. This is unreasonably expensive.

SUMMARY OF THE INVENTION

It is therefore an object of the present invention to provide a roentgenogram image capturing apparatus for capturing a roentgenogram image to produce a digital image data and systematically store a large amount of the digital image data in a storage device to display the image on the screen thereby making it possible to save space for the preservation of a large number of roentgenogram films. The roentgenogram image capturing apparatus thus constructed can search for the desired roentgenogram image with ease. Furthermore, unlike the roentgenogram films, the digital image data on the roentgenogram image can be prevented from deteriorating thereby making it possible to keep the roentgenogram for a long time. Moreover, the roentgenogram image capturing apparatus can be constructed without investment in new peculiar equipment, such as a new expensive digital X-ray image capturing system, thereby making it possible to cut costs.

It is another object of the present invention to provide a roentgenogram image capturing method of capturing a roentgenogram image to produce a digital image data and systematically store a large amount of the digital image data in a storage device to display the image on the screen thereby making it possible to save space for the preservation of a large number of roentgenogram films. In the roentgenogram image capturing method, the desired roentgenogram image can be retrieved from the storage device with ease. Furthermore, unlike the roentgenogram films, the digital image data on the roentgenogram image can be prevented from deteriorating thereby making it possible to keep the roentgenogram for a long time. Moreover, the roentgenogram image capturing method can cut costs because no need to invest in new peculiar equipment, such as a new expensive digital X-ray image capturing system.

It is a further object of the present invention to provide a computer program product for capturing a roentgenogram image to produce a digital image data and systematically store a large amount of the digital image data in a storage device to display the image on the screen thereby making it possible to save space for the preservation of a large number of roentgenogram films. The computer program product can search for the desired roentgenogram image with ease. Furthermore, unlike the roentgenogram films, the digital image data on the roentgenogram image can be prevented from deteriorating thereby making it possible to keep the roentgenogram for a long time. Moreover, the computer program product can cut costs because no need to invest in new peculiar equipment, such as a new expensive digital X-ray image capturing system.

It is a yet further object of the present invention to provide a roentgenogram image capturing system for capturing a roentgenogram image to produce a digital image data and systematically store a large amount of the digital image data in a storage device to display the image on the screen thereby making it possible to save space for the preservation of a large number of roentgenogram films. The roentgenogram image capturing system thus constructed can search for the desired roentgenogram image with ease. Furthermore, unlike the roentgenogram films, the digital image data on the roentgenogram image can be prevented from deteriorating thereby making it possible to keep the roentgenogram for a long time. Moreover, the roentgenogram image capturing system can cut costs and save space for the preservation of a large number of roentgenogram films. Moreover, the computer program product can cut costs because no need to invest in new peculiar equipment, such as a new expensive digital X-ray image capturing system.

In accordance with a first aspect of the present invention, there is provided a roentgenogram image capturing apparatus for capturing a roentgenogram image, comprising: a film projector having a front panel for holding a roentgenogram film of a predetermined part of patient's body thereon, for projecting the roentgenogram image of the roentgenogram film on the front panel; an image capturing unit disposed in face-to-face relationship with and spaced apart from at a predetermined distance the front panel of the film projector, for capturing the roentgenogram image projected on the front panel of the film projector to produce a digital image data on the roentgenogram image in accordance with a photography instruction; and an image processing unit for processing the digital image data. The image processing unit has: (a) transmitting means for sending the photography instruction to the image capturing unit and receiving the digital image data from the image capturing unit; (b) displaying means for displaying the roentgenogram image on a predetermined roentgenogram viewer screen on the basis of the digital image data; (c) a storage device capable of storing therein the digital image data on a plurality of the roentgenogram images; and (d) identifying means for identifying the digital image data on the plurality of the roentgenogram images with the patients by corresponding respective identifiers to sort the plurality of the digital image data by the patient to store the sorted digital image data in the storage device.

In the above roentgenogram image capturing apparatus, the image processing unit may be disposed near to the film projector. Moreover, the image processing unit further has selecting means for selecting one from among the plurality of patients, and retrieving means for retrieving the digital image data on the roentgenogram image on the basis of the identifier corresponding to the selected patient. The image processing unit is operable to have the displaying means display thereon the roentgenogram image on the basis of the digital image data retrieved by the retrieving means. Moreover, the identifying means of the image processing unit is operable to identify parts of the patient's body with predetermined identifiers.

In accordance with a second aspect of the present invention, there is provided a roentgenogram image capturing method of capturing a roentgenogram image, comprising the steps of:

(a) preparing a film projector having a front panel for holding a roentgenogram film of a predetermined part of patient's body thereon, for projecting the roentgenogram image of the roentgenogram film on the front panel, and an image capturing unit disposed in face-to-face relationship with and spaced apart from at a predetermined distance the front panel of the film projector, for capturing the roentgenogram image projected on the front panel of the film projector to produce a digital image data on the roentgenogram image in accordance with a photography instruction;

(b) sending the photography instruction to the image capturing unit;

(c) making the image capturing unit produce the digital image data on the roentgenogram image in response to the photography instruction;

(d) receiving the digital image data from the image capturing unit;

(e) displaying the roentgenogram image on a predetermined roentgenogram viewer screen on the basis of the digital image data;

(f) identifying the digital image data on the plurality of the roentgenogram images with the patients by corresponding respective identifiers to sort the plurality of the digital image data by the patient; and (g) storing the sorted digital image data in a predetermined storage device.

The above roentgenogram image capturing method may further comprise the steps of disposing the image processing unit near to the film projector, and making the image processing unit perform the steps (b), and (d) to (g).

The above roentgenogram image capturing method may further comprise the steps of:

(b) selecting one from among the plurality of patients; and (i) retrieving the digital image data on the roentgenogram image on the basis of the identifier corresponding to the selected patient, wherein the step (e) having the step of displaying thereon the roentgenogram image on the basis of the digital image data retrieved in the step (i). Moreover, the step (f) may have the step of identifying parts of the patient's body with predetermined identifiers.

In accordance with a third aspect of the present invention, there is provided a computer program product comprising a computer usable storage medium having computer readable code embodied therein for capturing a roentgenogram image projected on a roentgenogram film projector having a front panel for holding a roentgenogram film of a predetermined part of patient's body thereon, for projecting the roentgenogram image of the roentgenogram film on the front panel, the front panel of the roentgenogram film projector being disposed in face-to-face relationship with and spaced apart from an image processing unit at a predetermined distance, the image processing unit for capturing the roentgenogram image projected on the front panel of the film projector to produce a digital image data on the roentgenogram image in accordance with a photography instruction, wherein the computer readable code comprising:

a first program product code for sending the photography instruction to the image capturing unit;

a second program product code for receiving the digital image data from the image capturing unit;

a third program product code for displaying the roentgenogram image on a predetermined roentgenogram viewer screen on the basis of the digital image data;

a fourth program product code for identifying the digital image data on the plurality of the roentgenogram images with the patients by corresponding respective identifiers to sort the plurality of the digital image data by the patient; and a fifth program product code for storing the sorted digital image data in a predetermined storage device.

The above computer readable code may further comprise: a sixth program product code for selecting one from among the plurality of patients; and a seventh program product code for retrieving the digital image data on the roentgenogram image on the basis of the identifier corresponding to the selected patient. The third program product code may further has a program product code for displaying thereon the roentgenogram image on the basis of the digital image data retrieved by the seventh program product code. Moreover, the fourth program product code may has a program product code for identifying parts of the patient's body with predetermined identifiers.

In accordance with a fourth aspect of the present invention, there is provided a roentgenogram image capturing system for capturing a roentgenogram image, comprising: a host computer, at least a roentgenogram image capturing apparatus linked with each other through a predetermined network, for capturing the roentgenogram image to produce a digital image data on the roentgenogram image; a storage device linked with the host computer and the roentgenogram image capturing apparatus and capable of storing therein a plurality of the digital image data on the roentgenogram images; transmitting means for transmitting the digital image data on the roentgenogram image from the roentgenogram image capturing apparatus to the storing means through the network, thereby making it possible to share the digital image data on the roentgenogram image between the host computer and the roentgenogram image capturing apparatus; and displaying means for displaying the roentgenogram image on a predetermined roentgenogram viewer screen on the basis of the digital image data.

The aforesaid roentgenogram image capturing apparatus may have: a film projector having a front panel for holding a roentgenogram film of a predetermined part of patient's body thereon, for projecting the roentgenogram image of the roentgenogram film on the front panel; an image capturing unit disposed in face-to-face relationship with and spaced apart from at a predetermined distance the front panel of the film projector, for capturing the roentgenogram image projected on the front panel of the film projector to produce a digital image data on the roentgenogram image in accordance with a photography instruction; and an image processing unit for processing the digital image data. The image processing unit of the roentgenogram image capturing apparatus may have: transmitting means for sending the photography instruction to the image capturing unit and receiving the digital image data from the image capturing unit; and identifying means for identifying the digital image data on the plurality of the roentgenogram images with the patients by corresponding respective identifiers to sort the plurality of the digital image data by the patient to store the sorted digital image data in the storage device.

The above roentgenogram image capturing system may further comprise: selecting means for selecting one from among the plurality of patients; and retrieving means for retrieving the digital image data on the roentgenogram image on the basis of the identifier corresponding to the selected patient from the storage device. The displaying means may be operated to display thereon the roentgenogram image on the basis of the digital image data retrieved by the retrieving means.

The storage device is capable of storing a medical record information to be shared between the host computer and the roentgenogram image capturing apparatus.

The aforesaid roentgenogram image capturing system may further comprise a terminal computer linked with the host computer through the network, the terminal computer having displaying means for displaying the roentgenogram image on the basis of the shared digital image data on a predetermined roentgenogram viewer screen.

The above identifying means of the image processing unit of the roentgenogram image capturing apparatus is operable to identify parts of the patient's body with predetermined identifiers.

BRIEF DESCRIPTION OF THE DRAWINGS

The present invention and many of the advantages thereof will be better understood from the following detailed description when considered in connection with the accompanying drawings, wherein:

FIG. 7 is a schematic view of the roentgenogram images during the image processing in the step S8 of the flowchart shown in FIG. 6;

FIG. 8 is a perspective view of a second preferred embodiment of the roentgenogram image capturing system according to the present invention;

DESCRIPTION OF THE PREFERRED EMBODIMENTS

Figure 1:
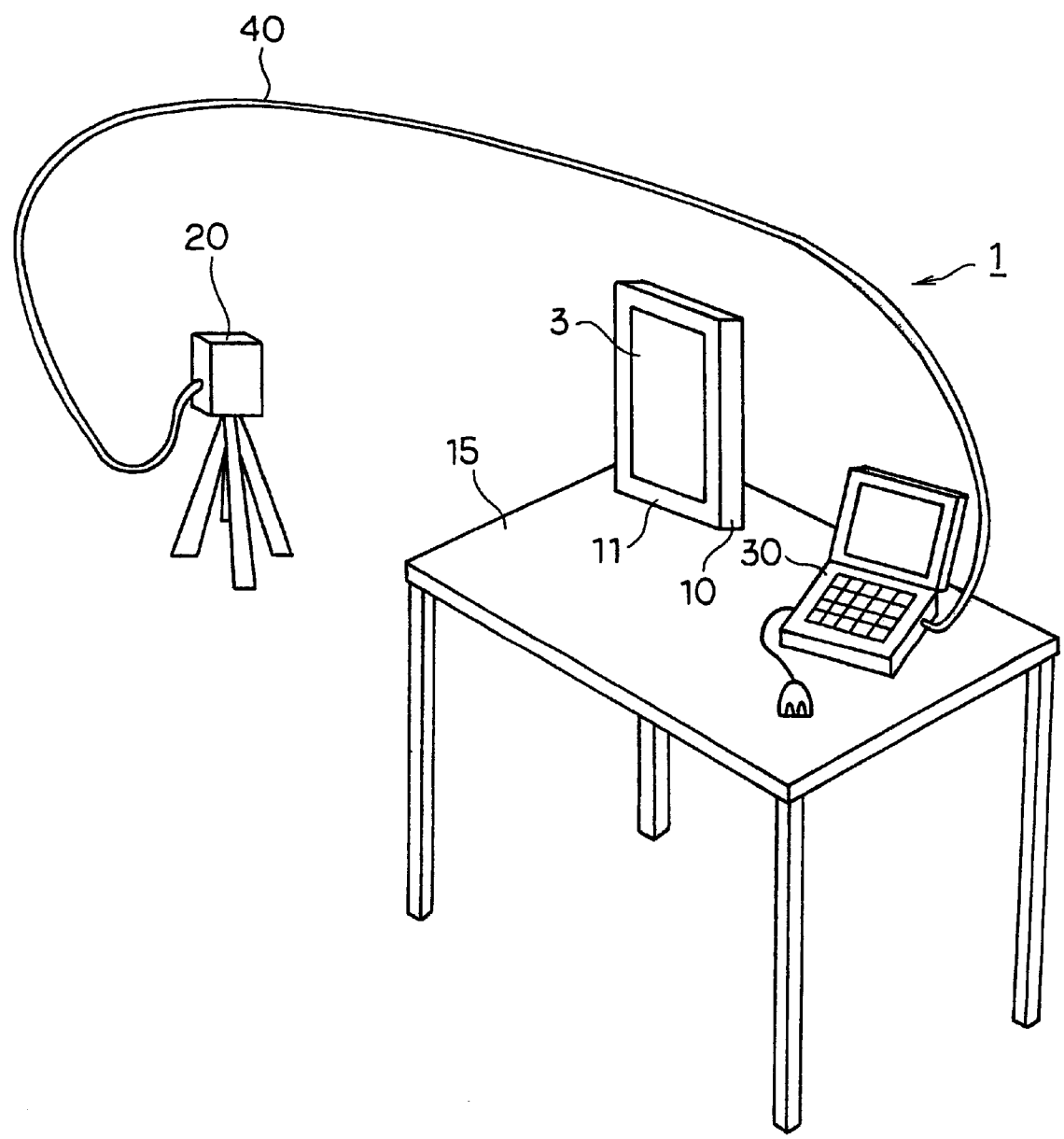
FIG. 1 is a perspective view of a first preferred embodiment of the roentgenogram image capturing apparatus according to the present invention.

Referring now to FIG. 1 of the drawings, there is best shown a first preferred embodiment of the roentgenogram image capturing apparatus according to the present invention. As shown in FIG. 1, the roentgenogram image capturing apparatus 1 comprises a typical diagnostic type of roentgenogram film projector 10, an image capturing unit 20, such as a general digital video camera and a general digital camera, stood apart from the roentgenogram film projector 10, and an image processing unit 30, such as a typical personal computer. The roentgenogram film projector 10 and the image processing unit 30 are disposed near to each other on a work table 15. The doctor can therefore handle both of the roentgenogram film projector 10 and the image processing unit 30 by himself while he is examining the patient.

The roentgenogram film projector 10 is designed to emit a light to an exposed and developed roentgenogram film 3 of a predetermined part of patient's body to project a roentgenogram image thereon. The diagnostic type of conventional roentgenogram film projector may be used as the roentgenogram film projector 10 of the roentgenogram image capturing apparatus according to the present invention. Therefore, it is unnecessary to invest in new equipment for projecting the roentgenogram image of the roentgenogram film. The image capturing unit 20 is designed to capture the roentgenogram image projected on the roentgenogram film projector 10 to produce a digital image data on the projected roentgenogram image. The image processing unit 30 is electrically connected to the image capturing unit 20 through a cable 40 and designed to input the digital image data from the image capturing unit 20 through the cable 40, to store therein a plurality of the inputted digital image data on the roentgenogram images and to identify the digital image data on the plurality of the roentgenogram images with the corresponding patients to sort the plurality of the digital image data by the patient to store the sorted digital image data.

Figure 2:
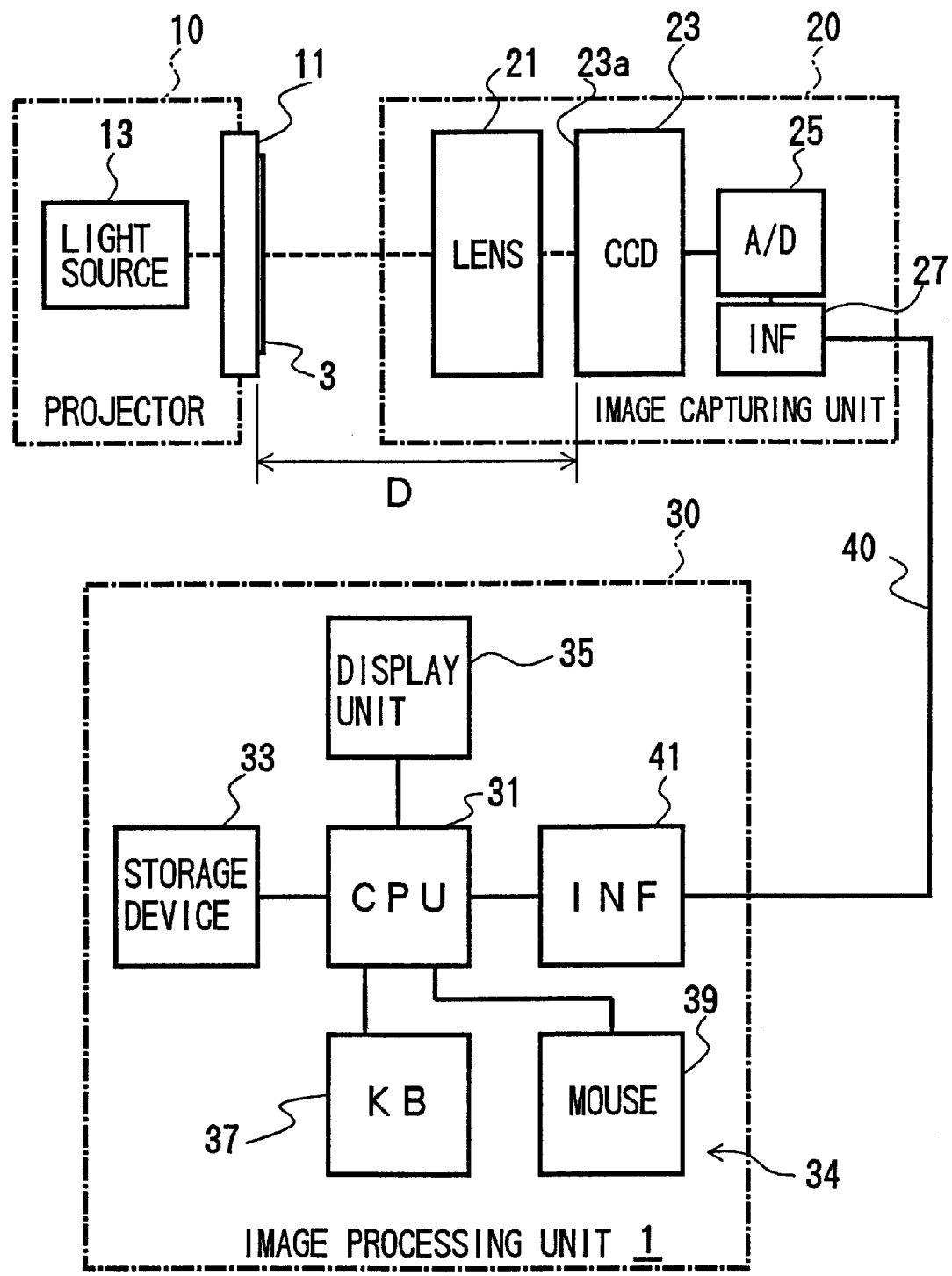
FIG. 2 is a block schematic diagram showing the roentgenogram image capturing apparatus shown in FIG. 1.

Referring to FIG. 2 of the drawings, there is shown a block schematic diagram illustrating the roentgenogram image capturing apparatus 1 shown in FIG. 1. As shown in FIG. 2, the roentgenogram film projector 10 comprises a front panel 11 for holding the exposed and developed roentgenogram film 3 of the predetermined patient's part thereon, and a light source 13 disposed behind the front panel 11 for emitting a light to the roentgenogram film 3 to project a roentgenogram image of the roentgenogram film 3 on the front panel 11.

The image capturing unit 20 comprises an optical lens 21 and an image sensor 23, such as a charge coupled device (CCD) sensor, adapted to sense the light passing through the optical lens 21 to focus into an image on an image formation surface 23a. The optical lens 21 of the image capturing unit 20 is stood face to face with the front panel 11 of the roentgenogram film projector 10. The image formation surface 23a of the image sensor 23 of the image capturing unit 20 is spaced apart from the front panel 11 of the roentgenogram film projector 10 at a predetermined interval "D" enough to focus the roentgenogram image on the image formation surface 23a of the image sensor 23 of the image capturing unit 20. The image capturing unit 20 further comprises an analog-to-digital converter 25, referred to as "A/D" in FIG. 2, which is designed to convert an electrical signal corresponding to the image formed on the image formation surface 23a to a digital image data, and an interface unit 27, referred to as "INF" in FIG. 2, which is designed to transmit the digital image data to a predetermined peripheral device, i.e., the image processing unit 30, therethrough.

The image processing unit 30 comprises a central processing unit 31, referred to as "CPU", a storage device 33, an operator console unit 34 including, but not limited to, a display unit 35, a keyboard 37, referred to as "KB" in FIG. 2, a mouse 39, and so on, and an interface unit 41, referred to as "INF" in FIG. 2.

The CPU 31 is designed to execute a predetermined roentgenogram image capturing program under a predetermined operating system to control the operation of the roentgenogram image capturing apparatus 1. The roentgenogram image capturing program is recorded in a computer usable storage medium, not shown in the drawings, such as a floppy disk, a CD-ROM, a DVD-ROM, a hard disk, and so on, having computer readable code embodied therein for capturing a roentgenogram image. The detailed description of the roentgenogram image capturing program will be made later in order to explain a computer program product according to the present invention. The CPU 31 can be electrically connected with a diversity of peripheral devices, such as the storage device 33, the operator console unit 34, the interface unit 41 and so on, by way of a bus. The CPU 31 is then operable to control the peripheral devices in accordance with the program.

The storage device 33 may include a random access memory (RAM) and a hard disk having a mass storage capacity enough to store therein a large amount of the digital image data transmitted from the image capturing unit 20 as well as the predetermined program and data which are used by the CPU 31. The RAM is capable of temporally storing data therein and serves as a work area for the CPU 31. The digital image data is formatted into a predetermined image file, for example, a Graphic Interchange Format file, a Joint Photographic Experts Group Format file, a bit map file, and so on.

The operator console unit 34 is adapted to allow an operator, e.g., a doctor, to operate the roentgenogram image capturing apparatus 1. The operator can operate the roentgenogram image capturing apparatus 1 by entering a predetermined data and/or instruction to the roentgenogram image capturing apparatus 1 through the keyboard 37 and the mouse 39 while the operator monitors a diversity of information and the roentgenogram image displayed on the screen of the display unit 35. There are provided with a diversity of graphical user interface (GUI) screens to be displayed on the display unit 35, so that the operator can operate the roentgenogram image capturing apparatus 1 with more ease. The description of the screens will be made later.

The interface unit 41 is adapted to electrically connect the image processing unit 30 and a predetermined external peripheral device, i.e., the image capturing unit 20, thereby making it possible for the image processing unit 30 to communicate with the external peripheral device.

In this embodiment, the image capturing unit 20 is electrically connected to the image processing unit 30 through the cable 40, such as a serial transmitting cable, to transmit the digital image data from the image capturing unit 20 to the image processing unit 30 through the cable 40, and to have a predetermined command and data transmitted between the image capturing unit 20 and the image processing unit 30. Thus, the image capturing unit 20 can be controlled by the image processing unit 30 in accordance with the command transmitted from the image processing unit 30, while the image processing unit 30 can receive data indicative of the information on the condition of the image capturing unit 20 from the image capturing unit 20. For instance, the image processing unit 30 is operable to transmit a photography command to the image capturing unit 20. The image capturing unit 20 is operable to take a photo of the roentgenogram film 3 to produce the digital image data on the roentgenogram image in accordance with the photography command transmitted from the image processing unit 30. The digital image data on the roentgenogram image is then transmitted from the image capturing unit 20 to the image processing unit 30 through the cable 40.

Alternatively, the digital image data may be transmitted between the image capturing unit 20 and the image processing unit 30 by way of a wireless communication interface unit. Alternatively, part of the image processing unit 30 may have the image capturing unit 20 built-in.

In another embodiment, the image capturing unit 20 may additionally comprise a storage device adapter, not shown, for making a predetermined removable mass storage media receive the static digital image data from the CCD sensor 23 to save this static digital image data thereon. In this case, the interface unit 41 of the image processing unit 30 may be a storage device adapter for inputting the digital image data from the removable mass storage media in the image processing unit 30 therethrough. In this case, the image processing unit 30 needs no cable 40 for connecting with the image capturing unit 20.

In another embodiment, the image capturing unit 20 may be the digital or analog video camera electrically connected to the image processing unit 30 through a video cable, while the image processing unit 30 may comprise a video inputting adapter for inputting a video signal from the image capturing unit 20. Then the image processing unit 30 can display the animation of the roentgenogram image real time on the screen of the display unit 35 and to allow the operator to select a static image from the animation to produce a static digital image data.

Figure 3:
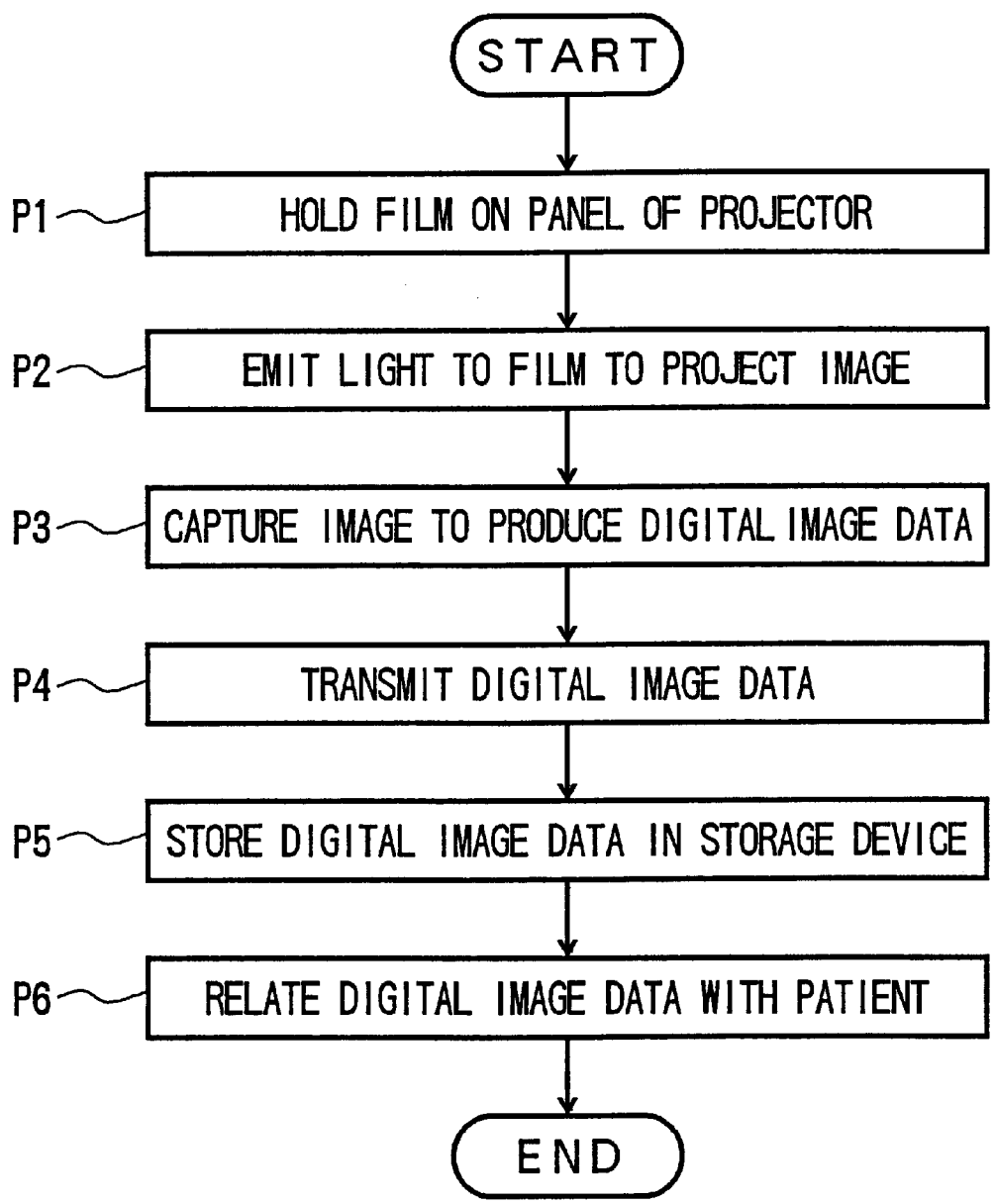
FIG. 3 is a flowchart showing the flow of processes of the roentgenogram image capturing method according to the present invention.

Referring now to FIG. 3 of the drawings, there is shown a method of capturing a roentgenogram image according to the present invention. As shown in FIG. 3, the method of capturing the roentgenogram image comprises the processes of P1 to P6. In the process P1, the roentgenogram film 3 of a predetermined patient is held on the front panel 11 of the roentgenogram film projector 10. In the following process P2, the light is emitted to the roentgenogram film 3 to project a roentgenogram image on the front panel 11 of the roentgenogram film projector 10. In the following process P3, the roentgenogram image is captured by the image capturing unit 20 to produce a digital image data on the roentgenogram image. In the following process P4, the digital image data on the roentgenogram image is transmitted from the image capturing unit 20 to the image processing unit 30. As described above, the digital image data on the roentgenogram image may be transmitted by way of a suitable transmitting medium, such as a cable, a wireless communication unit, a storage device adapter, and so on.

In the following process P5, the transmitted digital image data on the roentgenogram image is stored in the storage device 33 of the image processing unit 30. In the following process P6, the digital image data on a plurality of the roentgenogram images are identified with the corresponding patient by corresponding respective identifiers to sort the plurality of the digital image data by the patient to store the sorted digital image data in the storage device 33 of the image processing unit 30.

Figure 4:
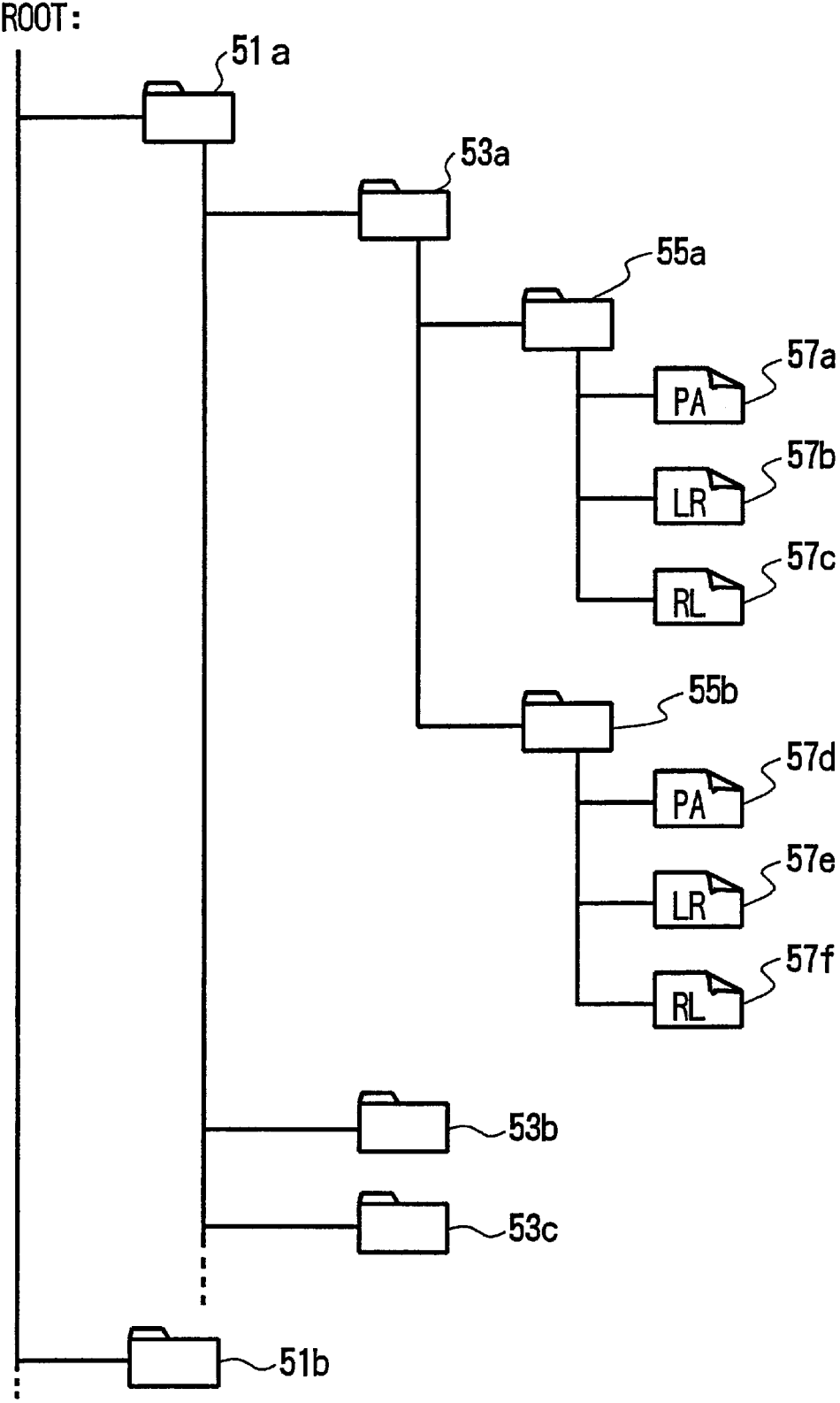
FIG. 4 is a schematic view of an example of the configuration of the folders created in the storage device of the roentgenogram image capturing apparatus shown in FIG. 1.

In this embodiment, the above process P6 has the step of creating a plurality of folders having a hierarchical structure and each having a name identifiable as a diversity of roentgenogram information, such as a patient identification code (ID), a patient name, a target part of the roentgenogram, a situation of the target part of the roentgenogram, a date, a time or the like. FIG. 4 shows a schematic view of an example of the configuration of the above folders created in the storage device 33 of the roentgenogram image capturing apparatus 1 according to the present invention. The hierarchical structure of the storage device 33 can make the plurality of digital image data sorted by the above roentgenogram information.

In this embodiment, the hierarchical structure has: first stage folders 51a, 51b, . . . , positioned below a root directory, and each having a name, for instance, "thoracicoabdominal part X-ray" and "abdominal part X-ray", identifiable as the target part to be examined by the roentgenography; second stage folders 53a, 53b, 53c, . . . , positioned below the first stage folders 51a, 51b, . . . , but not shown in FIG. 4, and each having a name identifiable as the patient and including the patient ID, such as a medical record number, and/or name; and third stage folders 55a, 55b, . . . , positioned below the second stage folders 53a, 53b, 53c, . . . and each having a name identifiable as the date and time. Each of the third folders 55a and 55b has a plurality of image data files 57a, 57b, . . . , and 57f, . . . , each having a name identifiable as the situation of the target part of the photography, for example, a PA (frontal view), an LR (left lateral view), and an RL (right lateral view).

For instance, in FIG. 4, the folders 51a, 53a, and 55a bear names of "thoracicoabdominal part X-ray", "78123_Taro Imaichi", and "1998-04-22_1628", respectively. The folder 55a has files 57a, 57b and 57c having names of "PA", "LR", and "RL", respectively, stored therein. This means that the digital image data of the files 57a, 57b and 57c stored in the folder 55a are the roentgenograms of Mr. Taro Imaichi's thoracicoabdominal part taken from the frontal view, the left lateral view, and the right lateral view, respectively, at 16:28 on Apr. 22, 1998. The folders 53b and 53c bear names of "860213_Hanako Nikko" and "990013_Jiro Kinugawa", respectively. This means that the digital image data on the roentgenograms of Ms. Hanako Nikko and Mr. Jiro Kinugawa are stored as the files, not shown, in the folders positioned below the folders 53b and 53c, respectively.

The digital image data on the roentgenogram thus stored in the folder can be related with the information identifiable with the target part, the patient, and the date and time, and so on with accuracy as well as with ease. Even if there is a large amount of the digital image data on the roentgenograms to be stored, the structure of the folders is simple, thereby making it possible to manage a large amount of the digital image data on the roentgenograms without mistakes.

Figure 5:
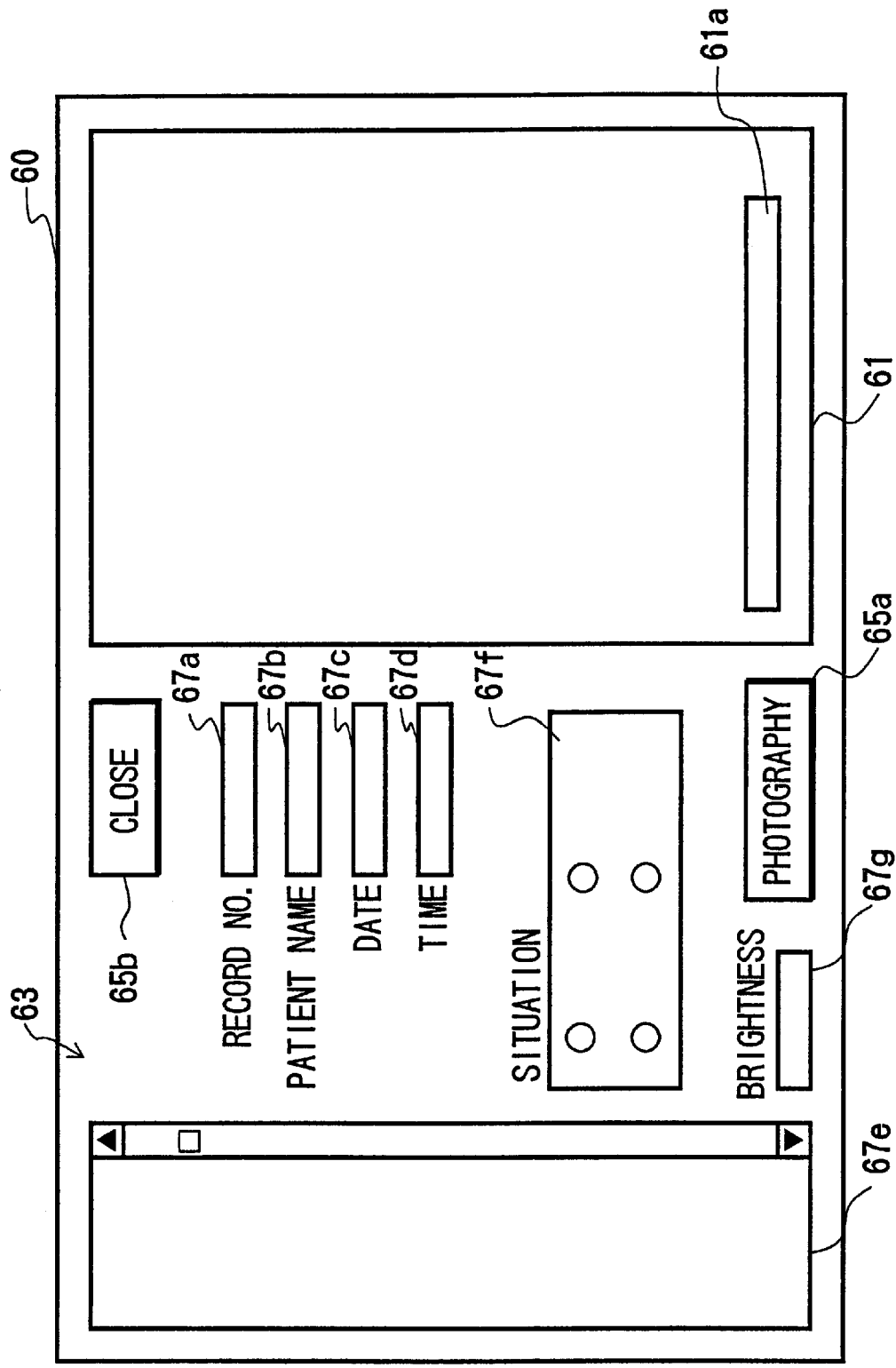
FIG. 5 is a schematic view of an example of the roentgenogram viewer screen displayed on the display unit of the roentgenogram image capturing apparatus shown in FIG. 1.

In this embodiment, there are a plurality of GUI screens for the operator. Referring to FIG. 5, there is shown a schematic view of an example of the roentgenogram viewer screen 60 displayed on the display unit 35 of the roentgenogram image capturing apparatus 1 according to the present invention.

As shown in FIG. 5, the roentgenogram viewer screen 60 includes a roentgenogram image display area 61, and an operation menu area 63. The roentgenogram image display area 61 has the roentgenogram image displayed therein on the basis of the digital image data transmitted from the image capturing unit 20 to the image processing unit 30. The operation menu area 63 is adapted to allow the operator to operate the roentgenogram image capturing apparatus 1 to serve as a man-machine interface.

The operation menu area 63 has a plurality of instruction buttons including a photography button 65a and a close button 65b. When the operator clicks the photography button 65a by way of the mouse 39, the image processing unit 30 is operated to send the photography command to the image capturing unit 20 to instruct the image capturing unit 20 to photograph the roentgenogram image to produce the digital image data on the roentgenogram image. The image processing unit 30 is then operated to receive the digital image data on the roentgenogram image from the image capturing unit 20. When the operator clicks the close button 65b by way of the mouse 39, the roentgenogram viewer screen 60 is closed. The roentgenogram viewer screen 60 may further has a memorization instruction button for saving the digital image data onto a predetermined memory area in the storage device 33. The digital image data is then saved on the storage device 33 in response to the operation of the memorization instruction button. The aforesaid instruction buttons may be icons, menus, commands, and so forth. These instruction buttons may be predetermined keys of the keyboard 37 to instruct predetermined commands in response to the operations of the corresponding keys of the keyboard 37, respectively.

The operation menu area 63 further has a plurality of data inputting fields for allowing the operator to input data by way of the keyboard 37 and the mouse 39. The data inputting fields may include a record number field 67a, a patient name field 67b, a date field 67c, a time field 67d, a patient name list 67e, a target part and situation selection area 67f, a brightness level field 67g, and so on. The operator can enter the information in each of the fields in the roentgenogram viewer screen 60. The patient name list 67e may be used for confirming that the patient's names which have been entered to store the digital image data of the roentgenogram image in the storage device 33 of the image capturing unit 30 already, thereby making it possible to prevent from repeatedly entering the patient's name.

The roentgenogram image display area 61 has a film information area 61a corresponding to a label area of the roentgenogram film 3 printing thereon a diversity of film information such as a patient ID, a patient name, a date and time of photography, a part and situation of photography, an age of the patient, a distinction of sex of the patient, and so on. Therefore, the operator can confirm that the roentgenogram image can be captured successfully. In another embodiment, the roentgenogram image capturing apparatus 1 may comprise a typical OCR (optical character reader) for scanning the film information in the film information area 61a to automatically produce a digital data on the film information. The digital data on the film information may be displayed on the corresponding fields in the operation menu area 63 of the roentgenogram viewer screen 60, so that the operator can confirm the information, and if necessary, correct the data by directly entering the data into the fields in the operation menu area 63 of the roentgenogram viewer screen 60. The digital image data on the roentgenogram image of the roentgenogram film 3 can be related with the patient and the film information on the basis of the information obtained as described above, and then stored in the storage device 33. The automatic production of the digital image data on the roentgenogram film will achieve the automatic successive photography of the roentgenogram films.

Figure 6:
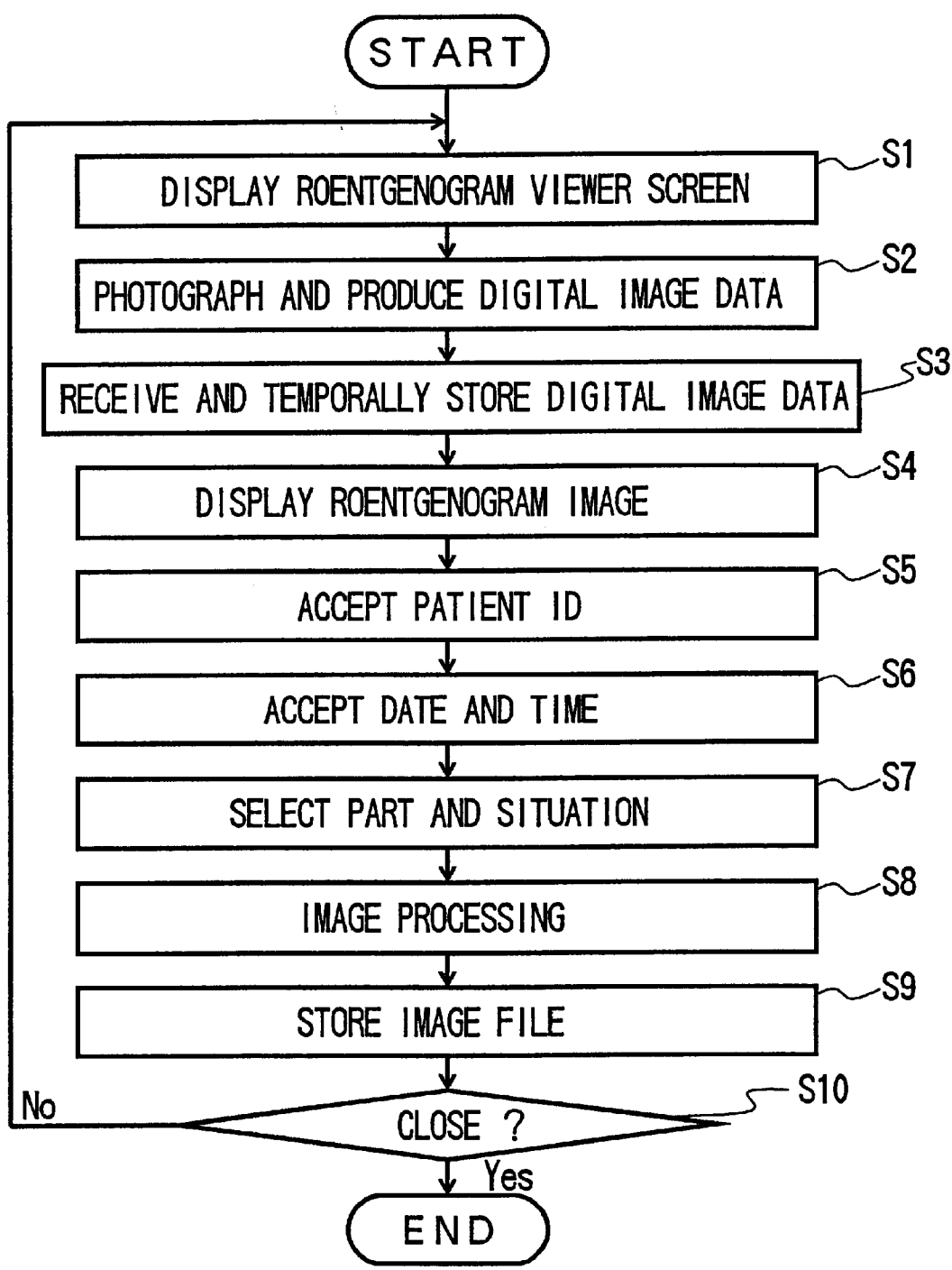
FIG. 6 is a flowchart of the program of capturing the roentgenogram image according to the present invention.

Referring now to FIG. 6 of the drawings, there is shown a flowchart of the program of capturing the roentgenogram image. The description of the computer program product according to the present invention will be made hereinlater. As shown in FIG. 6, the program of capturing the roentgenogram image comprises the steps of S1 to S9.

In the step S1, the image processing unit 30 is operated to display a predetermined screen including the aforesaid roentgenogram viewer screen 60 on the display unit 35. The image processing unit 30 is then operated to enter the wait state for predetermined instructions made by the operator. In the following step S2, the image processing unit 30 is operated to instruct the image capturing unit 20 to photograph the roentgenogram image of the roentgenogram film 3 projected on the roentgenogram film projector 10 in response to the operation of the photography button 65a of the roentgenogram viewer screen 60. More specifically, the image processing unit 30 is operated to issue the photography command to the image capturing unit 20 through the cable 40, when the operator clicks the photography button 65a. The image processing unit 30 is then operated to enter the wait state for the response from the image capturing unit 20. The image capturing unit 20 is then operated to photograph the roentgenogram film 3 and to produce the digital image data to transmit the digital image data to the image processing unit 30 through the cable 40.

In the following step S3, the image processing unit 30 is operated to receive and temporally store the transmitted digital image data in the storage device 33. In the step S4, the image processing unit 30 is operated to display the roentgenogram image on the roentgenogram image display area 61 of the roentgenogram viewer screen 60 on the basis of the digital image data transmitted from the image capturing unit 20.

Throughout the following steps S5 to S7, the image processing unit 30 is operated to enter the wait state for the instruction made by the operator. More specifically, in the step S5, the image processing unit 30 is operated to allow the operator to input the patient ID into the record number field 67a of the roentgenogram viewer screen 60 by way of the keyboard 37 to specify the patient. The patient ID may be represented by a medical record number of the patient indicated by letters, numbers, symbols and combination thereof. In response to the input of the patient ID, the image processing unit 30 is operated to retrieve the patient name from a predetermined patient list previously stored in the storage device 33 to display the patient name on the field 67b of the roentgenogram viewer screen 60. Alternatively, the patient name may be directly inputted to the field 67b or selected by using the patient name list 67e.

In the step S6, the image processing unit 30 is operated to allow the operator to input the date and time of the roentgenogram film 3 into the fields 67c and 67d of the roentgenogram viewer screen 60 by way of the keyboard 37. In the step S7, the image processing unit 30 is operated to allow the operator to select one of check buttons in the situation selection area 67f of the roentgenogram viewer screen 60 by way of the mouse 39, so that the roentgenogram image can be specified in its body part and its situation.

In another embodiment, the inputted data, such as the patient ID, the date and time of the roentgenogram film 3, and the body part and situation of the roentgenogram image, may be automatically scanned and converted from the data in the film information area 61a of the roentgenogram image display area 61 by the OCR as described above in the steps S5 to S7. In another embodiment, the steps S5 to S7 may be performed prior to the steps S2 to S4.

In the step S8, the image processing unit 30 is, if necessary, operated to perform predetermined image processing having the steps of: controlling the brightness of the roentgenogram image 71 received from the image processing unit 20 in the step S3 in accordance with the level specified by the operator by entering the brightness level in the brightness level field 67g of the roentgenogram viewer screen 60; and rotating the roentgenogram image 73 by predetermined degrees to produce an end roentgenogram image 75 as shown in FIG. 7.

The image processing unit 30 may further perform the image processing having the steps of compensating the gamma of the image, adjusting the contrast of the image, and compressing the data on the image. Alternatively, the property of the image processing may have been previously determined and the image processing is then automatically performed in accordance with the predetermined property whenever the digital image data is transmitted from the image capturing unit 20. In another embodiment, the image processing processes may be achieved by using a general image processing software.

Returning to FIG. 6 of the drawings, in the step S9, the image processing unit 30 is operated to search the storage device 33 for the folders corresponding to the digital image data on the roentgenogram image received from the image capturing unit 20. When there is no corresponding folder, the image processing unit 30 is operated to create a folder within the storage device 33 and a suitable named image file as described above and then to save the image file on the corresponding folder within the storage device 33.

The steps S1 to S9 can be repeatedly performed to capture a plurality of the images. In the step S10, the judgment is made whether the close button 65b is operated or not. When the answer is "YES", this program is terminated to close the roentgenogram viewer screen 60. When the answer is "NO", the step S10 is returned to the step S1. Furthermore, the confirmation that the digital image data has been already saved may be made before the program is terminated. The digital image data is, if necessary, saved before the program is terminated.

Alternatively, the program for capturing the roentgenogram image according to the present invention may be programmed to be executable by a predetermined multitask system computer.

The operation of the roentgenogram image capturing apparatus 1 will be described hereinlater.

When the image processing unit 30, i.e., the personal computer, starts to execute the program for capturing the roentgenogram image according to the present invention, the roentgenogram viewer screen 60 is displayed on the display unit 35. At this time, the image processing unit 30 is waiting for a predetermined instructions made by the operator. The roentgenogram film 3 is held on the front panel 11 of the roentgenogram film projector 10. When the operator clicks the photography button 65*a* by the mouse 37, the image capturing unit 20 is operated to photograph the roentgenogram film 3 to transmit the digital image data to the image processing unit 30 through the cable 40.

When the digital image data on the roentgenogram image is received by the image processing unit 30, the roentgenogram image is displayed on the roentgenogram image display area 61 of the roentgenogram viewer screen 60 on the basis of the digital image data transmitted from the image capturing unit 20.

The operator then enters the patient ID into the record number field 67*a* of the roentgenogram viewer screen 60 by way of the keyboard 37 to specify the corresponding patient. The patient name is automatically indicated in the patient name field 67*b*. Alternatively, the operator may select a single name of the patient from the patient name list 67*e* including all patients in the hospital and previously entered. In this case, the patient ID and the patient name are automatically indicated in the record number field 67*a* and the patient name field 67*b*, respectively. The operator then enters the date and time in the fields 67*c* and 67*d*, respectively, by way of the keyboard 37.

The operator clicks one of check buttons in the situation selection area 67*f* of the roentgenogram viewer screen 60 by way of the mouse 39 to select the part and situation of the corresponding roentgenogram image.

After the image processing of the roentgenogram image, the digital image data on the roentgenogram image is saved as the image file on the corresponding folder in the storage device 33. When the roentgenogram film is replaced with another one, the aforesaid processes are repeated.

When the operator intends to see the specific roentgenogram image, the operator enters the patient ID into the record number field 67*a* of the roentgenogram viewer screen 60 by way of the keyboard 37 to specify the desired patient. The image processing unit 30 is operated to search the storage device 33 for the image file of the roentgenogram image corresponding to the specified patient. In this embodiment, as described above, the image file of the roentgenogram image corresponding to the specified patient is stored in the folder named the patient name. When the desired image file can be found, the roentgenogram image and the corresponding film information are displayed on the roentgenogram viewer screen 60. At this time, the operator can select the part and situation of the roentgenogram image by selecting the check button in situation selection area 67*f* of the roentgenogram viewer screen 60 by way of the mouse 39. The image processing unit 30 is then operated to search the corresponding folder for the image file of the roentgenogram image corresponding to the specified part and situation. When the desired image file can be found, the roentgenogram image and the corresponding film information are displayed on the roentgenogram viewer screen 60. Furthermore, the operator can specify the date and/or time of the roentgenogram image by entering the date and/or time in the fields 67*c* and/or 67*d* of the roentgenogram viewer screen 60 by way of the keyboard 37.

This means that the operator can specify a desired patient ID, patient name, date, time, part and/or situation of the roentgenogram film to make the image processing unit 30 retrieve the image file of a desired roentgenogram film from the storage device 33 to display the corresponding roentgenogram image on the display unit 35.

It will be understood from the above description that the roentgenogram image capturing apparatus, method and computer program product according to the present invention can capture a roentgenogram image to produce a digital image data and systematically store a large amount of the digital image data in a storage device to display the image on the screen and search for the desired roentgenogram image with ease. Furthermore, unlike the roentgenogram films, the digital image data on the roentgenogram image can be prevented from deteriorating thereby making it possible to keep the roentgenogram for a long time. Moreover, the roentgenogram image capturing apparatus, method and computer program product can cut costs and save space for the preservation of a large number of roentgenogram films.

Figure 9:
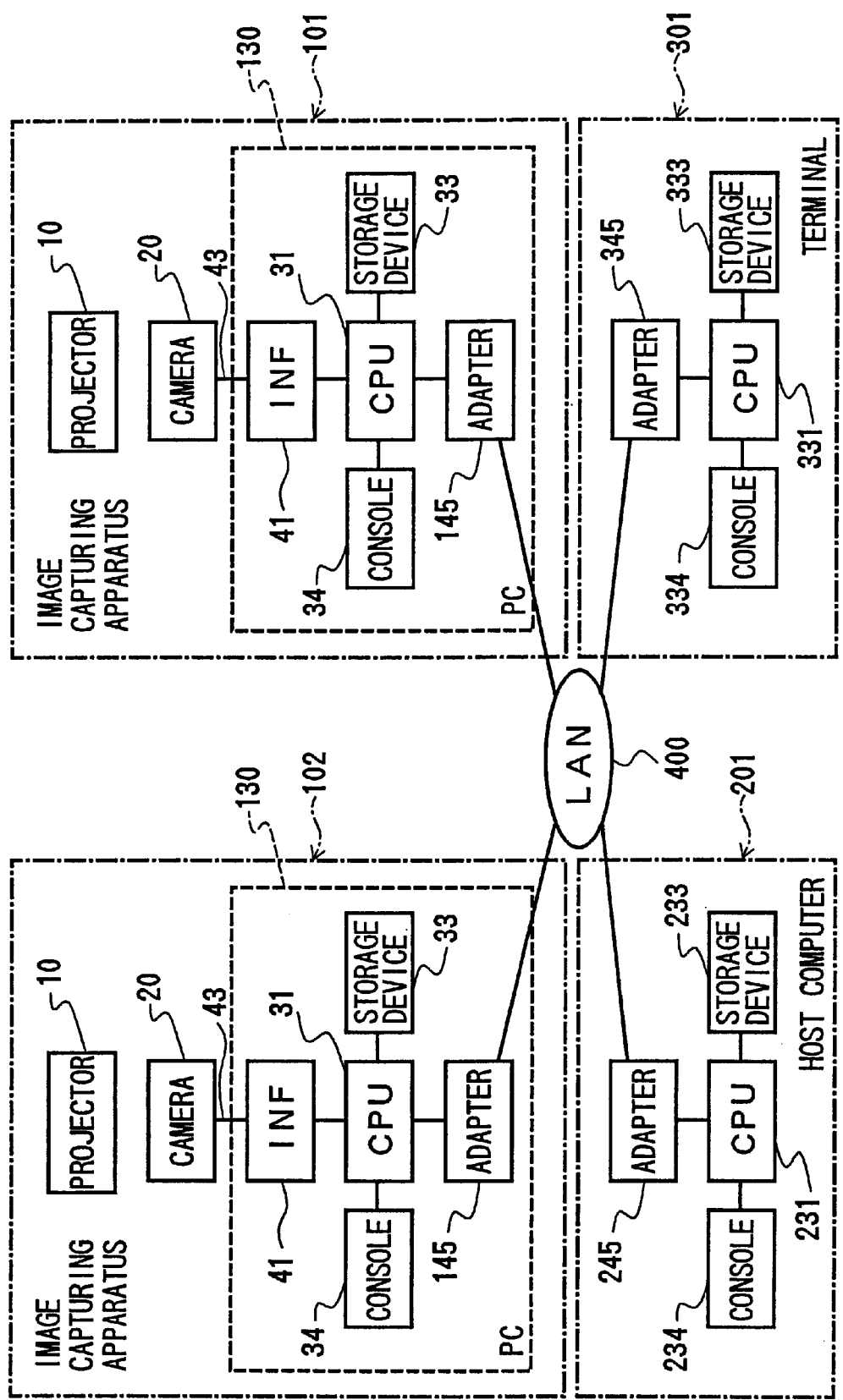
FIG. 9 is a block schematic diagram showing the roentgenogram image capturing system shown in FIG. 8.
Figure 10:
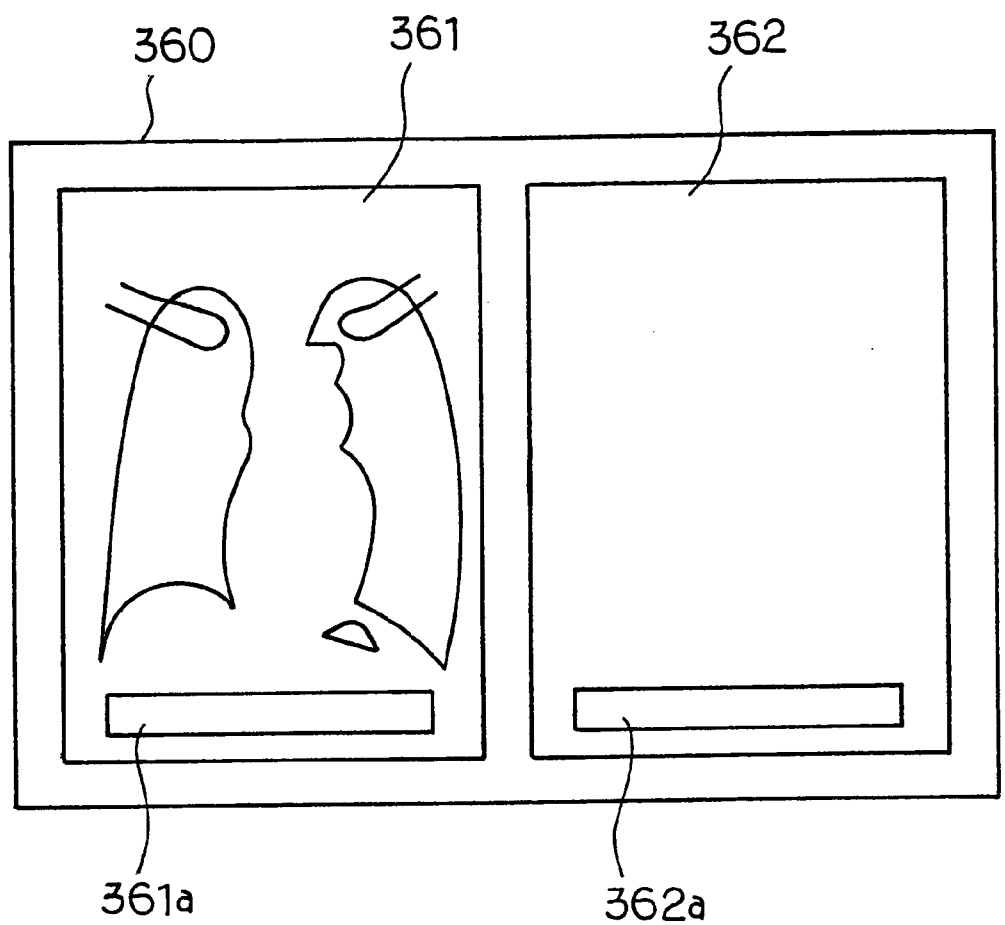
FIG. 10 is a schematic view of an example of the medical record information screen displayed on the display unit of the terminal computer shown in FIG. 8.

The roentgenogram image capturing apparatus according to the present invention can be thus constituted of the conventional film projector and the general digital camera in cooperation with the typical personal computer without investing in a new large-scale system. The roentgenogram image capturing apparatus according to the present invention can be therefore provided with ease and low cost. Furthermore, the doctor can confirm that the patient ID printed on the roentgenogram film corresponds to the patient whom the doctor is examining, thereby preventing mistake of inputting another patient ID, because of the fact that both of the roentgenogram film projector and the image processing unit are disposed on the work table and can be thus handled by the doctor. Referring to FIGS. 8 to 10 of the drawings, there is shown a second prefer red embodiment of the roentgenogram image capturing system according to the present invention. FIG. 8 is a perspective view of the roentgenogram image capturing system. The second embodiment of the roentgenogram image capturing system comprises first and second roentgenogram image capturing apparatuses 101 and 102, a host computer 201, and a terminal computer 301, all of them being linked with each other through a predetermined network 400, such as a LAN (Local Area Network).

The first and second roentgenogram image capturing apparatuses 101 and 102 are respectively adapted to capture the roentgenogram image of the roentgenogram film 3 and 3' to produce the digital image data to be shared through the network 400. The first and second roentgenogram image capturing apparatuses 101 and 102, the host computer 201 and the terminal computer 301 thus linked through the LAN 400 can be controlled under a predetermined network operating system to share a resource with each other.

Each of the first and second roentgenogram image capturing apparatuses 101 and 102 comprises the roentgenogram film projector 10, the image capturing unit 20, and an image processing unit 130, such as a typical personal computer. The projector 10 and the image capturing unit 20 of each of the first and second roentgenogram image capturing apparatuses 101 and 102 are the same as those of the roentgenogram image capturing apparatus 1 of the first embodiment shown in FIG. 1. These same constitutional elements are simply represented by the same reference numerals as those of the first embodiment, and will be thus omitted in description for avoiding tedious repetition.

The host computer 201 serves as a typical server and is adapted to control all of the devices linked to the network 400 to share the resources including the digital image data on the roentgenogram image and the film information with each other.

The terminal computer 301 may be a typical personal computer. The terminal computer 301 is capable of retrieving the digital image data on the roentgenogram image and the film information from the resources by way of the network 400.

Referring to FIG. 9 of the drawings, there is shown a block schematic diagram of the roentgenogram image capturing system shown in FIG. 8.

The image processing unit 130 of each of the first and second roentgenogram image capturing apparatuses 101 and 102 comprises a network adapter unit 145 in addition to the image processing unit 30 of the roentgenogram image capturing apparatus 1 shown in FIG. 1 and the same constitutional elements, including the CPU 31, the storage device 33, the operator console unit 34, and the interface unit 41, same as those of the first embodiment shown in FIG. 2. These same constitutional elements are simply represented by the same reference numerals as those of the first embodiment, and will be thus omitted in description for avoiding tedious repetition.

The network adapter unit 145 is designed to make it possible for the image processing unit 130 to communicate with the other devices linked to the network 400.

The host computer 201 comprises a CPU 231, a storage device 233, an operator console unit 234 including, but not limited to, a display unit, a keyboard, a mouse, and so on, and a network adapter unit 245.

The CPU 231 is designed to execute a predetermined program under a predetermined operating system. The CPU 231 is electrically connected to a plurality of peripheral devices including the storage device 233, the operator console unit 234 and the network adapter 245 through a bus. The CPU 231 is then operable to control the peripheral devices in accordance with the program.

The storage device 233 may include a RAM and a hard disk having a mass storage capacity enough to store therein a large amount of the digital image data captured by and transmitted from the first and second roentgenogram image capturing apparatuses 101 and 102 as well as the predetermined program and data which are used by the CPU 231. The RAM is capable of temporally storing data therein and serves as a work area for the CPU 231.

The hard disk of the storage device 233 is further capable of storing a diversity of medical record information therein. The host computer 201 thus constructed can centralize a diversity of medical record information as well as the digital image data on the roentgenogram films. Here, the medical record information may include an admission plane, a discharge process summary, an admission process graph, an endoscopic image, an ultrasonogram, a computed tomographic image, an electrocardiogram, a photography during operation, an ophthalmography, and so on. Alternatively, the medical record information may be stored in another storage device in the existing computer system, not shown, linked to the network 400.

The operator console unit 234 is adapted to allow an operator to operate the host computer 201. The operator can operate the host computer 201 by entering a predetermined data and/or instruction to host computer 201 through its keyboard and mouse while the operator monitors a diversity of information and the roentgenogram image displayed on the screen of its display unit. There are provided with a diversity of GUI screens to be displayed on the display unit, so that the operator can operate the host computer 201 with more ease.

The network adapter unit 245 is designed to make it possible for the host computer 201 to communicate with the other devices linked to the network 400.

The terminal computer 301 comprises a CPU 331, a storage device 333, an operator console unit 334, and a network adapter unit 345. The CPU 331 is designed to execute a predetermined program under a predetermined operating system. The CPU 331 is electrically connected to a plurality of peripheral devices including the storage device 333, the operator console unit 334 and the network adapter 345 through a bus. The CPU 331 is then operable to control the peripheral devices in accordance with the program.

The storage device 333 may include a hard disk and a RAM. The hard disk is capable of storing therein the predetermined program and data which are used by the CPU 331. The RAM is capable of temporally storing data therein and serves as a work area for the CPU 331.

The operator console unit 334 is adapted to allow an operator to operate the terminal computer 301. The operator can operate the terminal computer 301 by entering a predetermined data and/or instruction to terminal computer 301 through its keyboard and mouse while the operator monitors a diversity of information and the roentgenogram image displayed on the screen of its display unit. There are provided with a diversity of GUI screens to be displayed on the display unit, so that the operator can operate the terminal computer 301 with more ease.

The network adapter unit 345 is designed to make it possible for the terminal computer 301 to communicate with the other devices linked to the network 400.

The description of the operation of the roentgenogram image capturing system of the second embodiment will be made hereinlater.

Firstly, the roentgenogram films 3 and 3' are held on the roentgenogram film projectors 10 of the first and second roentgenogram image capturing apparatuses 101 and 102, respectively. The roentgenogram image of the roentgenogram films 3 and 3' are then captured by the image capturing units 20 of the first and second roentgenogram image capturing apparatuses 101 and 102 to produce the digital image data on the roentgenogram image, respectively. In each of the first and second roentgenogram image capturing apparatuses 101 and 102, the digital image data on the roentgenogram image is then transmitted from the image capturing unit 20 to the image processing unit 130. These operations of the first and second roentgenogram image capturing apparatuses 101 and 102 are the same as that of the roentgenogram image capturing apparatus 1 of the first embodiment. The digital image data on the roentgenogram image is then transmitted from each of the first and second roentgenogram image capturing apparatuses 101 and 102 to the host computer 201 through the network adapter unit 145 via the network 400. The transmitted digital image data on the roentgenogram image is stored in the storage device 233 of the host computer 201, accordingly, the digital image data on the roentgenogram image can be shared with the terminal computer 301 as well as the roentgenogram image capturing apparatuses 101 and 102. This means that the operator can use the terminal computer 301 anywhere but linked with the network 400 to refer the roentgenogram image to efficiently examine the patient.

Referring to FIG. 10 of the drawings, there is shown a schematic diagram of an example of a predetermined medical record information screen 360 displayed on the display units of the first and second roentgenogram image capturing apparatuses 101 and 102, the terminal computer 301 and the host computer 201. As shown in FIG. 10, the medical record information screen 360 includes a roentgenogram image display area 361, and a medical record information area 362.

The roentgenogram image display area 361 has the roentgenogram image displayed therein on the basis of the digital image data on the roentgenogram image stored in the storage device 233 of the host computer 201. The medical record information area 362 has a diversity of information on the patient.

In particular, the roentgenogram image display area 361 and the medical record information area 362 have a film information area 361*a* and a patient information area 362*a*, respectively. The film information area 361*a* of the roentgenogram image display area 361 corresponds to a label area of the roentgenogram film printing thereon a diversity of film information such as a patient ID, a patient name, a date and time of photography, a part and situation of photography, an age of the patient, a distinction of sex of the patient, and so on. The patient information area 362*a* of the medical record information area 362 includes a patient ID (a medical record number), a name of the patient, an age of the patient, a distinction of sex of the patient, and so on.

It will be understood from the above description, the roentgenogram image capturing system according to the present invention can capture a roentgenogram image to produce a digital image data and systematically store a large amount of the digital image data in a storage device to display the image on the screen and search for the desired roentgenogram image with ease. Furthermore, unlike the roentgenogram films, the digital image data on the roentgenogram image can be prevented from deteriorating thereby making it possible to keep the roentgenogram for a long time. Moreover, the roentgenogram image capturing system can cut costs and save space for the preservation of a large number of roentgenogram films without installing a new expensive digital X-ray image capturing system.

It will be apparent to those skilled in the art and it is contemplated that variations and/or changes in the embodiments illustrated and described herein may be without departure from the present invention. Accordingly, it is intended that the foregoing description is illustrative only, not limiting, and that the true spirit and scope of the present invention will be determined by the appended claims.

What is claimed is:

1. A roentgenogram image capturing apparatus for capturing a roentgenogram image, comprising:
    a film projector having a front panel for holding a roentgenogram film of a predetermined part of patient's body thereon, for projecting said roentgenogram image of said roentgenogram film on said front panel;
    an image capturing unit disposed in face-to-face relationship with and spaced apart from at a predetermined distance said front panel of said film projector, for capturing the roentgenogram image projected on said front panel of said film projector to produce a digital image data on said roentgenogram image in accordance with a photography instruction; and
    an image processing unit for processing said digital image data, having:
        (a) transmitting means for sending said photography instruction to said image capturing unit and receiving said digital image data from said image capturing unit;
        (b) displaying means for displaying said roentgenogram image on a predetermined roentgenogram viewer screen on the basis of said digital image data;
        (c) a storage device capable of storing therein said digital image data on a plurality of said roentgenogram images; and
        (d) identifying means for identifying said digital image data on said plurality of said roentgenogram images with said patients by corresponding respective identifiers to sort said plurality of said digital image data by said patient to store the sorted digital image data in said storage device.

2. The roentgenogram image capturing apparatus as set forth in claim 1, wherein said image processing unit is disposed near to said film projector.

3. The roentgenogram image capturing apparatus as set forth in claim 1, wherein said image processing unit further has selecting means for selecting one from among said plurality of patients, and retrieving means for retrieving said digital image data on said roentgenogram image on the basis of the identifier corresponding to the selected patient, said image processing unit being operable to have said displaying means display thereon the roentgenogram image on the basis of the digital image data retrieved by said retrieving means.

4. The roentgenogram image capturing apparatus as set forth in claim 1, wherein said identifying means of said image processing unit is operable to identify parts of said patient's body with predetermined identifiers.

5. A roentgenogram image capturing method of capturing a roentgenogram image, comprising the steps of:
    (a) preparing a film projector having a front panel for holding a roentgenogram film of a predetermined part of patient's body thereon, for projecting said roentgenogram image of said roentgenogram film on said front panel, and an image capturing unit disposed in face-to-face relationship with and spaced apart from at a predetermined distance said front panel of said film projector, for capturing the roentgenogram image projected on said front panel of said film projector to produce a digital image data on said roentgenogram image in accordance with a photography instruction;
    (b) sending said photography instruction to said image capturing unit;
    (c) making said image capturing unit produce said digital image data on said roentgenogram image in response to said photography instruction;
    (d) receiving said digital image data from said image capturing unit;
    (e) displaying said roentgenogram image on a predetermined roentgenogram viewer screen on the basis of said digital image data;
    (f) identifying said digital image data on said plurality of said roentgenogram images with said patients by corresponding respective identifiers to sort said plurality of said digital image data by said patient; and
    (g) storing the sorted digital image data in a predetermined storage device.

6. The roentgenogram image capturing method as set forth in claim 5, further comprising the steps of disposing said image processing unit near to said film projector, and making said image processing unit perform the steps (b), and (d) to (g).

7. The roentgenogram image capturing method as set forth in claim 5, further comprising the steps of:
    (h) selecting one from among said plurality of patients; and
    (i) retrieving said digital image data on said roentgenogram image on the basis of the identifier corresponding to the selected patient, wherein the step (e) having the step of displaying thereon the roentgenogram image on the basis of the digital image data retrieved in the step (i).

8. The roentgenogram image capturing method as set forth in claim 5, wherein the step (f) having the step of identifying parts of said patient's body with predetermined identifiers.

9. A computer program product comprising a computer usable storage medium having computer readable code embodied therein for capturing a roentgenogram image projected on a roentgenogram film projector having a front panel for holding a roentgenogram film of a predetermined part of patient's body thereon, for projecting said roentgenogram image of said roentgenogram film on said front panel, said front panel of said roentgenogram film projector being disposed in face-to-face relationship with and spaced apart from an image processing unit at a predetermined distance, said image processing unit for capturing the roentgenogram image projected on said front panel of said film projector to produce a digital image data on said roentgenogram image in accordance with a photography instruction, wherein said computer readable code comprising:

a first program product code for sending said photography instruction to said image capturing unit;

a second program product code for receiving said digital image data from said image capturing unit;

a third program product code for displaying said roentgenogram image on a predetermined roentgenogram viewer screen on the basis of said digital image data;

a fourth program product code for identifying said digital image data on said plurality of said roentgenogram images with said patients by corresponding respective identifiers to sort said plurality of said digital image data by said patient; and a fifth program product code for storing the sorted digital image data in a predetermined storage device.

10. The computer program product as set forth in claim 9, wherein said computer readable code further comprising:

a sixth program product code for selecting one from among said plurality of patients; and a seventh program product code for retrieving said digital image data on said roentgenogram image on the basis of the identifier corresponding to the selected patient, wherein said third program product code having a program product code for displaying thereon the roentgenogram image on the basis of the digital image data retrieved by said seventh program product code.

11. The computer program product as set forth in claim 9, wherein said fourth program product code having a program product code for identifying parts of said patient's body with predetermined identifiers.

12. A roentgenogram image capturing system for capturing a roentgenogram image, comprising:

a host computer, at least a roentgenogram image capturing apparatus linked with each other through a predetermined network, for capturing said roentgenogram image to produce a digital image data on said roentgenogram image;

a storage device linked with said host computer and said roentgenogram image capturing apparatus and capable of storing therein a plurality of said digital image data on said roentgenogram images;

transmitting means for transmitting said digital image data on said roentgenogram image from said roentgenogram image capturing apparatus to said storing means through said network, thereby making it possible to share said digital image data on said roentgenogram image between said host computer and said roentgenogram image capturing apparatus; and displaying means for displaying said roentgenogram image on a predetermined roentgenogram viewer screen on the basis of said digital image data;

said roentgenogram image capturing apparatus having:

a film projector having a front panel for holding a roentgenogram film of a predetermined part of patient's body thereon, for projecting said roentgenogram image of said roentgenogram film on said front panel;

an image capturing unit disposed in face-to-face relationship with and spaced apart from at a predetermined distance said front panel of said film projector, for capturing the roentgenogram image projected on said front panel of said film projector to produce a digital image data on said roentgenogram image in accordance with a photography instruction; and an image processing unit for processing said digital image data, having:

(a) transmitting means for sending said photography instruction to said image capturing unit and receiving said digital image data from said image capturing unit; and (b) identifying means for identifying said digital image data on said plurality of said roentgenogram images with said patients by corresponding respective identifiers to sort said plurality of said digital image data by said patient to store the sorted digital image data in said storage device.

13. The roentgenogram image capturing system as set forth in claim 12, further comprises:

selecting means for selecting one from among said plurality of patients; and retrieving means for retrieving said digital image data on said roentgenogram image on the basis of the identifier corresponding to the selected patient from said storage device;

wherein said displaying means is operated to display thereon the roentgenogram image on the basis of the digital image data retrieved by said retrieving means.

14. The roentgenogram image capturing system as set forth in claim 12, wherein said storage device is capable of storing a medical record information to be shared between said host computer and said roentgenogram image capturing apparatus.

15. The roentgenogram image capturing system as set forth in claim 12, further comprising a terminal computer linked with said host computer through said network, said terminal computer having displaying means for displaying said roentgenogram image on the basis of said shared digital image data on a predetermined roentgenogram viewer screen.

16. The roentgenogram image capturing system as set forth in claim 12, wherein said identifying means of said image processing unit of said roentgenogram image capturing apparatus is operable to identify parts of said patient's body with predetermined identifiers.

* * * * *